US008771336B2

(12) United States Patent
Roeder

(10) Patent No.: US 8,771,336 B2
(45) Date of Patent: Jul. 8, 2014

(54) ENDOLUMINAL PROSTHESIS COMPRISING A VALVE REPLACEMENT AND AT LEAST ONE FENESTRATION

(75) Inventor: Blayne A. Roeder, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/335,115

(22) Filed: Dec. 22, 2011

(65) Prior Publication Data

US 2012/0197382 A1 Aug. 2, 2012

Related U.S. Application Data

(63) Continuation-in-part of application No. 13/213,349, filed on Aug. 19, 2011.

(60) Provisional application No. 61/375,815, filed on Aug. 21, 2010.

(51) Int. Cl.
*A61F 2/06* (2013.01)
*A61F 2/82* (2013.01)
(52) U.S. Cl.
USPC ............... 623/1.13; 623/1.31; 623/1.37
(58) Field of Classification Search
USPC ..................................... 623/1.13, 1.35
See application file for complete search history.

(56) References Cited

U.S. PATENT DOCUMENTS

| | | | |
|---|---|---|---|
| 1,597,525 A | 8/1926 | Knake | |
| 5,314,468 A | 5/1994 | Ramos Martinez | |
| 5,366,473 A | 11/1994 | Winston et al. | |
| 5,411,552 A | 5/1995 | Andersen et al. | |
| 5,425,765 A | 6/1995 | Tiefenbrun et al. | |
| 5,445,600 A | 8/1995 | Abdulla | |
| 5,603,698 A | 2/1997 | Roberts et al. | |
| 5,653,743 A | 8/1997 | Martin | |
| 5,662,703 A | 9/1997 | Yurek et al. | |
| 5,676,697 A | 10/1997 | McDonald | |
| 5,891,195 A | 4/1999 | Klostermeyer et al. | |
| 5,984,955 A | 11/1999 | Wisselink | |
| 6,086,526 A | 7/2000 | Francischelli | |

(Continued)

FOREIGN PATENT DOCUMENTS

| | | |
|---|---|---|
| EP | 1 673 039 | 6/2006 |
| EP | 1 847 234 B1 | 10/2007 |
| WO | WO 2005/034810 A1 | 4/2005 |

OTHER PUBLICATIONS

Extended European Search Report, EU App. No. 11178162.1 dated Jul. 17, 2012, 8 pgs.

(Continued)

*Primary Examiner* — Thomas J Sweet
*Assistant Examiner* — Tiffany Shipmon
(74) *Attorney, Agent, or Firm* — Brinks Gilson & Lione

(57) ABSTRACT

An endoluminal prosthesis comprises a graft having a tubular body comprising proximal and distal ends, and a valve replacement disposed between the proximal and distal ends of the graft. At least one stent is coupled to the graft and has a contracted delivery state and an expanded state for maintaining patency within a portion of the graft. At least one fenestration is disposed in a sidewall of the graft at a location distal to the valve replacement. In one embodiment, the at least one fenestration is pivotable in any direction away from an axis perpendicular to a longitudinal axis of the prosthesis.

16 Claims, 10 Drawing Sheets

(56) References Cited

U.S. PATENT DOCUMENTS

| | | |
|---|---|---|
| 6,344,052 B1 | 2/2002 | Greenan et al. |
| 6,395,018 B1 | 5/2002 | Castaneda |
| 6,482,228 B1 | 11/2002 | Norred |
| 6,514,286 B1 | 2/2003 | Leatherbury et al. |
| 6,524,335 B1 | 2/2003 | Hartley et al. |
| 6,544,285 B1 | 4/2003 | Thubrikar et al. |
| 6,942,879 B2 | 9/2005 | Humes |
| 7,393,360 B2 | 7/2008 | Spenser et al. |
| 7,442,204 B2 | 10/2008 | Schwammenthal et al. |
| 7,510,574 B2 | 3/2009 | Le et al. |
| 7,645,298 B2 | 1/2010 | Hartley et al. |
| 7,678,141 B2 | 3/2010 | Greenan et al. |
| 7,771,467 B2 | 8/2010 | Svensson |
| 8,016,877 B2 | 9/2011 | Seguin et al. |
| 2002/0052648 A1 | 5/2002 | McGuckin, Jr. et al. |
| 2002/0058992 A1 | 5/2002 | Greenhalgh |
| 2003/0023300 A1* | 1/2003 | Bailey et al. ............ 623/1.13 |
| 2003/0199967 A1 | 10/2003 | Hartley et al. |
| 2004/0034406 A1 | 2/2004 | Thramann |
| 2004/0059406 A1 | 3/2004 | Cully et al. |
| 2004/0106972 A1 | 6/2004 | Deaton |
| 2004/0215327 A1 | 10/2004 | Doig et al. |
| 2005/0102021 A1 | 5/2005 | Osborne |
| 2005/0131517 A1 | 6/2005 | Hartley et al. |
| 2005/0131518 A1 | 6/2005 | Hartley et al. |
| 2005/0149166 A1 | 7/2005 | Schaeffer et al. |
| 2005/0171597 A1 | 8/2005 | Boatman et al. |
| 2005/0171598 A1 | 8/2005 | Schaeffer |
| 2005/0182476 A1 | 8/2005 | Hartley et al. |
| 2005/0222668 A1 | 10/2005 | Schaeffer et al. |
| 2005/0222669 A1 | 10/2005 | Purdy |
| 2005/0222674 A1 | 10/2005 | Paine |
| 2005/0228488 A1 | 10/2005 | Nazzaro |
| 2005/0273155 A1 | 12/2005 | Bahler et al. |
| 2006/0058864 A1 | 3/2006 | Schaeffer et al. |
| 2006/0217802 A1 | 9/2006 | Ruiz et al. |
| 2006/0247760 A1 | 11/2006 | Ganesan et al. |
| 2007/0179592 A1 | 8/2007 | Schaeffer |
| 2007/0244547 A1 | 10/2007 | Greenan |
| 2007/0276468 A1 | 11/2007 | Holzer et al. |
| 2008/0275548 A1 | 11/2008 | Svensson |
| 2009/0012602 A1 | 1/2009 | Quadri |
| 2009/0030502 A1* | 1/2009 | Sun et al. ............ 623/1.16 |
| 2009/0182405 A1 | 7/2009 | Arnault de la Menardiere et al. |
| 2009/0240316 A1 | 9/2009 | Bruszewski |
| 2009/0259290 A1 | 10/2009 | Bruszewski |
| 2009/0264821 A1 | 10/2009 | Mafi et al. |
| 2009/0264991 A1* | 10/2009 | Paul et al. ............ 623/1.35 |
| 2010/0063576 A1 | 3/2010 | Schaeffer et al. |
| 2010/0268319 A1* | 10/2010 | Bruszewski et al. ......... 623/1.13 |
| 2010/0268327 A1 | 10/2010 | Bruszewski et al. |
| 2011/0054586 A1 | 3/2011 | Mayberry et al. |
| 2011/0166644 A1 | 7/2011 | Keeble et al. |

OTHER PUBLICATIONS

Reply to Extended European Search Report for EP12198788 filed Dec. 23, 2013, 17 pgs.
Patent Examination Report No. 1 for Australian Patent Application No. 2012268911 issued Apr. 3, 2013, 4 pgs.
Extended European Search Report for EP12198788 dated May 13, 2013, 7 pgs.
Amendment filed Mar. 4, 2014 for U.S. Appl. No. 13/213,349, 7 pgs.
Applicant Initiated Interview Summary dated Feb. 27, 2014 for U.S. Appl. No. 13/213,349, 3 pgs.
Office Action dated Dec. 3, 2013 for U.S. Appl. No. 13/213,349, 6 pgs.
RCE filed Nov. 19, 2013 for U.S. Appl. No. 13/213,349, 4 pgs.
Advisory Action dated Nov. 14, 2013, for U.S. Appl. No. 13/213,349, 3 pgs.
Amendment filed Oct. 21, 2013 for U.S. Appl. No. 13/213,349, 7 pgs.
Final Office Action dated Jun. 19, 2013 for U.S. Appl. No. 13/213,349, 6 pgs.
Supplemental Amendment and Statement of Substance of Interview dated Jun. 7, 2013 for U.S. Appl. No. 13/213,349, 7 pgs.
Applicant Initiated Interview Summary dated Jun. 5, 2013 for U.S. Appl. No. 13/213,349, 3 pgs.
Amendment dated May 3, 3013 for U.S. Appl. No. 13/213,349, 9 pgs.
Office Action dated Jan. 3, 2012 for U.S. Appl. No. 13/213,349, 8 pgs.

* cited by examiner

ENDOLUMINAL PROSTHESIS COMPRISING A VALVE REPLACEMENT AND AT LEAST ONE FENESTRATION

CROSS-REFERENCE TO RELATED APPLICATIONS

This application is a continuation-in-part of U.S. Utility patent application Ser. No. 13/213,349, filed Aug. 19, 2011 and entitled "Prosthesis Having Pivoting Fenestration," which claims priority to U.S. Provisional Patent Application Ser. No. 61/375,815, filed Aug. 21, 2010, each of which are incorporated herein by reference in their entirety.

BACKGROUND

The functional vessels of human and animal bodies, such as blood vessels and ducts, occasionally weaken or even rupture. For example, the aortic wall can weaken, resulting in an aneurysm, or it may develop a tear in one of the layers of the aortic wall resulting in an aortic dissection.

One common surgical intervention for weakened, aneurysmal or ruptured passageways or ducts involves the use of an endoluminal prosthesis to provide some or all of the functionality of the original, healthy passageway or duct and/or preserve any remaining vascular integrity by replacing a length of the existing passageway or duct wall that spans the site of failure or defect. Endoluminal prostheses may be of a unitary construction or may be comprised of multiple prosthetic modules. They also may be a single tubular device or a bifurcated branching device depending on the desired application.

In many cases, however, the damaged or defected portion of the vasculature may include a branch vessel branching from the main vessel. For example, in the case of the abdominal aorta, there are at least three major branch vessels, including the celiac, mesenteric, and renal arteries, as well as other others, leading to various other body organs. Thus, when the damaged portion of the vessel includes one or more of these branch vessels, some accommodation must be made to ensure that the prosthesis does not block or hinder blood flow through the branch vessel. In many instances, there may in insufficient healthy tissue in the aorta near the branching vessels adequately seal a prosthesis without partially or completely blocking one or more of the branching vessels.

SUMMARY

An endoluminal prosthesis comprises a graft having a tubular body comprising proximal and distal ends, and a valve replacement disposed between the proximal and distal ends of the graft. At least one stent is coupled to the graft and has a contracted delivery state and an expanded state for maintaining patency within a portion of the graft. At least one fenestration is disposed in a sidewall of the graft at a location distal to the valve replacement.

In one embodiment, the at least one fenestration is pivotable in any direction away from an axis perpendicular to a longitudinal axis of the prosthesis. There may be a first perimeter having a first diameter and surrounding the at least one fenestration, a band of flexible material attached to and surrounding the first perimeter and having a flexible frame, and a second perimeter attached to and surrounding the band of flexible material and having a second diameter greater than the first perimeter diameter. The band of material has a first diameter substantially the same as the first perimeter diameter and a second diameter substantially the same as the diameter of the second perimeter. The diameter of the band of material decreases in a direction away from the surface of the graft from the second perimeter to the first perimeter.

In exemplary embodiments, the band of material has a concave or convex orientation relative to the surface of the graft. The band of material may be configured to independently move between an interior surface of the graft and an exterior surface of the graft.

In one embodiment, first and second fenestrations may be disposed in the graft at locations between about 90 and about 270 degrees apart. A first branch vessel prosthesis may extend between the first fenestration and a right coronary artery in a deployed state, and a second branch vessel prosthesis may extend between the second fenestration and a left coronary artery in the deployed state.

The valve replacement may comprise an artificial valve having a tricuspid shape. The valve replacement may be located at the proximal end of the graft, and one or more barbs extend radially outward from the proximal end of the graft.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

Figure 1:
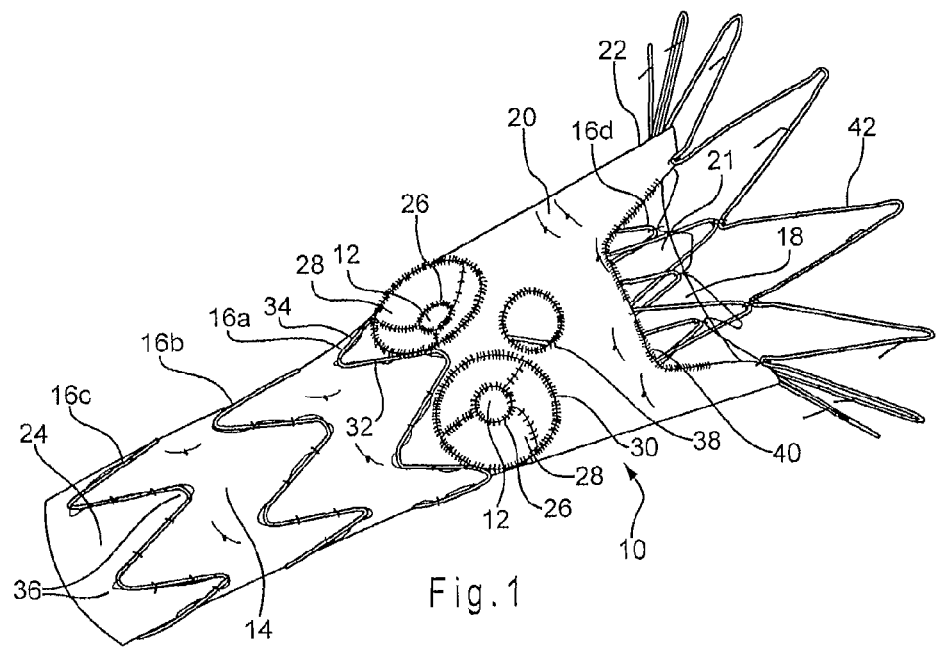
FIG. 1 shows a perspective view of a fenestrated prosthesis having pivotable fenestrations concave (internal) pivotable fenestrations.

The present disclosure relates to an endoluminal prosthesis, such as a stent graft that includes one or more fenestrations to accommodate endovascular disease, such as an aneurysm in cases where one or more side branches is involved, and a side branch prosthesis is deployed within the fenestration to permit fluid flow from the endoluminal prosthesis into the branch vessel. The prosthesis includes fenestrations that pivot as needed to accommodate the dynamic geometry of the aortic branches. In various aspects shown and described in more detail below, for example, one or more pivotable fenestrations provided on a prosthesis lie outside the surface plane of the body of the prosthesis and will allow a branch vessel stent, graft or stent-graft that has been placed in the fenestration to pivot into a variety of orientations required to meet and seal the branch vessel device in the branch vessel. The orientation of the fenestrations may dynamically change over time as needed by changing anatomy.

Unless defined otherwise, all technical and scientific terms used herein have the same meaning as commonly understood to one of ordinary skill in the art to which this invention belongs.

The term "distal" means a location or direction that is, or a portion of a device that when implanted is further downstream in the direction of or with respect to blood flow.

The term "proximal" means a location or direction that is, or a portion of a device that when implanted is further upstream in the direction of or with respect to blood flow.

The term "fenestration" means an opening provided through a surface of a prosthesis from the interior of the prosthesis to the exterior of the prostheses and may have a variety of geometries, including circular, semi-circular, oval, oblong, as well as other geometries.

The term "biocompatible" refers to a material that is substantially non-toxic in the in vivo environment of its intended use, and that is not substantially rejected by the patient's physiological system (i.e., is non-antigenic). Examples of biocompatible materials from which textile graft material can be formed include, without limitation, polyesters, such as polyethylene terephthalate; fluorinated polymers, such as polytetrafluoroethylene (PTFE) and fibers of expanded PTFE, and polyurethanes. In addition, materials that are not inherently biocompatible may be subjected to surface modifications in order to render the materials biocompatible. Examples of surface modifications include graft polymerization of biocompatible polymers on the materials surface, coating of the surface with a crosslinked biocompatible polymer, chemical modification with biocompatible functional groups, and immobilization of a compatibilizing agent such as heparin or other biocompatible substances. Thus, any fibrous material having sufficient strength to survive in the in vivo environment may be used to form a textile graft, provided the final textile is biocompatible. Fibers suitable for making textile grafts include polyethylene, polypropylene, polyaramids, polyacrylonitrile, nylon, and cellulose, in addition to the polyesters, fluorinated polymers, and polyurethanes as listed above. Furthermore, bioremodelable materials may also be used singly or in combination with the aforementioned polymer materials. The textile may be made of one or more polymers that do not require treatment or modification to be biocompatible. The graft may be constructed from woven multifilament polyester, for example and without limitation, Dacron™, produced by DuPONT. Dacron™ is known to be sufficiently biologically inert, non-biodegradable, and durable to permit safe insertion inside the human body.

The term "prosthesis" means any device for insertion or implantation into or replacement for a body part or function of that body part. It may also mean a device that enhances or adds functionality to a physiological system. The term prosthesis may include, for example and without limitation, a stent, stent-graft, filter, valve, balloon, embolization coil, and the like.

The term "tubular" refers to the general shape of an endoluminal device which allows the module to carry fluid along a distance or fit within a tubular structure such as an artery. Tubular prosthetic devices include single, branched, and bifurcated devices. Tubular may refer to any shape including, but not limited to, tapered, cylindrical, curvilinear, or any combination thereof. A tubular device may have a cross-sectional shape that is, circular, substantially circular or the like. However, it should be understood that the cross-sectional shape is not limited thereto, and other shapes, such as, for example, hexagonal, pentagonal, octagonal, or the like are contemplated. The term "endoluminal" refers to or describes objects that can be placed inside a lumen or a body passageway in a human or animal body. A lumen or a body passageway can be an existing lumen or a lumen created by surgical intervention. As used in this specification, the terms "lumen" or "body passageway" are intended to have a broad meaning and encompasses any duct (e.g., natural or iatrogenic) within the human body and can include a member selected from the group comprising: blood vessels, respiratory ducts, gastrointestinal ducts, and the like. "Endoluminal device" or "endoluminal prosthesis" thus describes devices that can be placed inside one of these lumens.

The term "graft" or "graft material" describes an object, device, or structure that is joined to or that is capable of being joined to or implanted in or against a body part to enhance, repair, or replace a portion or a function of that body part. A graft by itself or with the addition of other elements, such as structural components, may comprise an endoluminal prosthesis. The graft may be comprised of a single material, a blend of materials, a weave, a laminate, or a composite of two or more materials. The graft may be constructed from natural or organic materials, for example and without limitation, a biological scaffold or bioremodelable material, such as small intestine submucosa ("SIS"), which is commercially available by Cook Biotech, West Lafayette, Ind. The graft may also be constructed from a synthetic, for example and without limitation, a polymer. The graft may be formed from a single layer or multiple layers of material. In embodiments employing a plurality of layers of material, the layers may remain separate, or may be attached to each other through a secondary process such as sintering, curing, adhesives, and sutures or the like.

The term "stent" means any device or structure that adds rigidity, expansion force or support to a prosthesis. A stent is used to obtain and maintain the patency of the body passageway while maintaining the integrity of the passageway. Also, the stent may be used to form a seal. The stent may be located on the exterior of the device, the interior of the device, or both. A stent may be self-expanding, balloon-expandable or may have characteristics of both. A variety of other stent configurations are also contemplated by the use of the term "stent." The stents 16 may be comprised of a metallic material selected from stainless steel, silver, platinum, palladium, gold, titanium, tantalum, iridium, tungsten, cobalt, chromium, cobalt-chromium alloy 1058, cobalt-based 35N alloy, nickel-based alloy 625, a molybdenum alloy, a molybdenum alloy including about 0.4% to about 0.8% of lanthanum oxide ($Li_2O_3$), and a nickel-titanium alloy, such as nitinol, or other suitable materials as known in the art. The stents may be made of a wire, or may be laser or cannula cut, or manufactured by other known methods.

The term "yarn" refers to a length of a continuous thread or strand of one or more filaments or fibers, with or without twist, suitable for weaving, knitting or otherwise intertwining to form a textile fabric.

The term "branch vessel" refers to a vessel that branches off from a main vessel. Examples are the celiac and renal arteries which are branch vessels to the aorta (i.e., the main vessel in this context). As another example, the hypogastric artery is a branch vessel to the common iliac, which is a main vessel in this context. Thus, it should be seen that "branch vessel" and "main vessel" are relative terms.

"Longitudinally" refers to a direction, position or length substantially parallel with a longitudinal axis of a reference, and is the length-wise component of the helical orientation.

"Circumferentially" refers to a direction, position, or length that encircles a longitudinal axis of reference. The term "circumferential" is not restricted to a full 360° circumferential turn or to a constant radius.

The terms "patient," "subject," and "recipient" as used in this application refer to any animal, especially humans.

FIGS. 1-8 show a fenestrated prosthesis 10, here a stent graft, having a tubular body and comprising a biocompatible material, having one or more fenestrations 12 pivotable in any direction away from an axis perpendicular to a longitudinal axis of the prosthesis. The pivotable fenestrations 12 have a diameter extending from a sidewall of the graft. The pivotable fenestrations 12 include a first, inner perimeter 26 surrounding the fenestration 12 having a diameter, a band 28 of flexible material attached to and surrounding the first perimeter 26, and a second, outer perimeter 30 attached to and surrounding the band 28 of flexible material. The band 28 of material has a first diameter that is substantially the same as the diameter of the first perimeter 26, and a second diameter substantially the same as the second perimeter 30. The diameter of the band of material decreases in a direction away from the surface 20 of the graft 14 from the second perimeter to the first perimeter. The band of flexible material may include a flexible frame 48.

In some aspects, the fenestrated prosthesis 10 is intended for placement in the abdominal aorta and to accommodate vessels that branch from the aorta, for example, the renal arteries, and into which a branch vessel prosthesis may be placed. However, the fenestrated prosthesis 10 is not limited for use in the abdominal aorta but may be used in other vessels of the body from which other vessels branch, such as the ascending thoracic aorta, the descending thoracic aorta, as well as other body vessels.

FIG. 1 shows a perspective view of a prosthesis 10 that is a stent graft. The prosthesis 10 includes graft material 14 associated with one or more stents 16. The prosthesis 10 has a proximal end 22, a distal end 24, and a lumen 18 extending through the prosthesis 10 to permit passage of blood flow from the proximal end 22 to the distal end 24. The stents 16 may be placed on the external surface 20 and/or internal surface 21 of the graft material 14. In one particular embodiment, the prosthesis 10, such as that shown in FIG. 1, has external body stents 16a, 16b, and 16c, and at least one internal stent 16d. The internal stent 16d may be a sealing stent and placed at or near the proximal end 22 of the prosthesis 10 to seal the prosthesis 10 at the proximal end 22 to the walls of a blood vessel into which it has been placed. Additionally, or alternatively, depending on the location of the place of the prosthesis 10 or a particular need, a sealing stent 16d may be placed at either or both the proximal and distal ends 22, 24 of prosthesis 10. The prosthesis 10 also may include an attachment mechanism, for example, an attachment stent 42, at either or both ends of the prosthesis 10, to further secure the prosthesis 10 within the body vessel and prevent migration of the prosthesis 10.

As shown in FIG. 1, the prosthesis 10 has several openings or fenestrations that extend from the internal surface 21 to the external surface 20 of the graft material 14. The prosthesis 10 of FIG. 1 has two pivotable fenestrations 12, at least one non-pivotable fenestration 38, and a scallop 40. Here, the scallop 40 is placed at the proximal end of the prosthesis 10.

FIGS. 1-8 show various aspects and views of the prosthesis 10 having pivotable fenestrations 12. Pivotable fenestrations 12 have an inner perimeter 26 surrounding the fenestration 12, a band 28 surrounding the inner perimeter 26, and an outer perimeter 30 surrounding the band 28. As shown, the outer perimeter 30 diameter is greater than the band 28 diameter and the inner perimeter diameter 26. The inner perimeter 26, the band 28 and the outer perimeter 30 would be substantially concentric with one another if they were in the same plane, for example the surface plane of the graft. The inner perimeter 26, the band 28 and the outer perimeter 30 may form a hemispherical shape, resembling a dome, or a frustoconical cone extending from the surface of the graft material 14. The fenestration 12 is provided at the peak or top of the hemispherical shape or extension. In other embodiments, the band 28 may comprise a tapered, flexible tube extending from the outer perimeter 30 and the inner diameter 26.

Stents 16, for example those shown in the Figures may be, for example zig zag stents, also known has Z-stents, that comprise a series of struts 32, 34 connected by apices 36, although the type of stent used is not so limited. When Z-stents are used, a portion of the outer perimeter 30 of one or more of the fenestrations 12 may lie between adjacent struts 32, 34 of one of the stents 16. The stents 16 may be either self-expanding or balloon expandable. Preferably, they are self-expanding. However, a combination of self-expanding and balloon expandable stents also may be contemplated.

Figure 5:
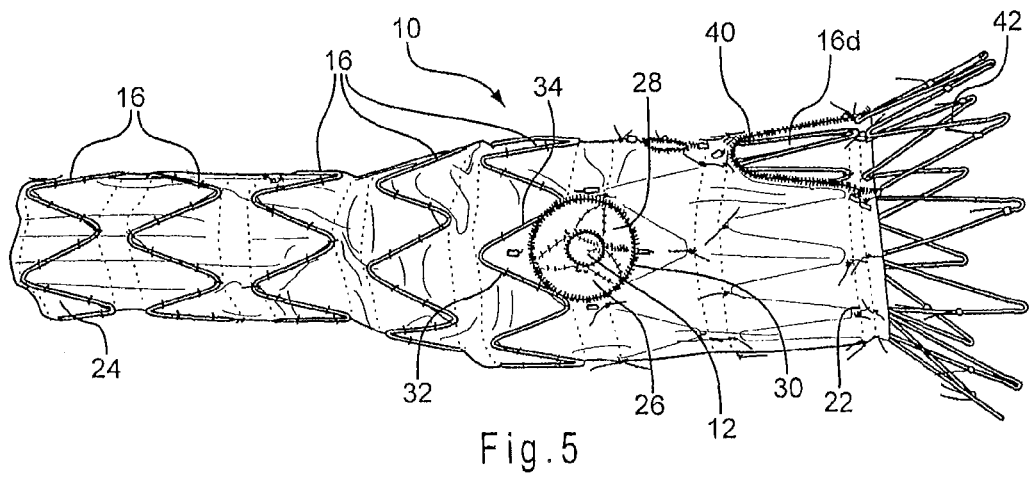
FIG. 5 shows another fenestrated prosthesis having pivotable fenestrations concave (internal) pivotable fenestrations.

As set forth above, the stents 16 include struts 32, 34 that are spaced apart from each other. The strut spacing is measured from bend-to-bend (or apex to apex 36). Stent amplitude, spacing and stagger are preferably optimized for each prosthesis design. In some aspects, the apices or bends 36 of the struts 32, 34 may be staggered for minimal contact with each other. As shown in FIG. 1, the stents 16a, 16b, 16c are positioned adjacent each other and the apices 36 of each row are in circumferential alignment with the bends of longitudinally adjacent rows. In other aspects, as shown in FIG. 5, every bend 36 of each row may be in substantial circumferential alignment with the bends 36 of longitudinally adjacent rows.

The pivotable fenestrations 12 may be located within the lumen 18 of the prosthesis 10 or extending from the exterior of the prosthesis 10. In the first aspect, the pivotable fenestrations 12 may be said to be concave, relative to the external surface 20 of the graft material 14. In the second aspect, the pivotable fenestrations 12 may be said to be convex, relative to the external surface 20 of the graft material 14. FIG. 1 shows the pivotable fenestrations 12 located internal to the prosthesis 10, that is, they lie within the lumen 18 of the prosthesis 10. In the particular aspect shown in FIG. 1, the pivotable fenestrations 12 reside substantially on one side of the prosthesis 10 and are adjacent to one another. In the aspects shown in FIGS. 3-4 and 7-8, the pivotable fenestrations 12 are positioned to align with, for example, the renal arteries. In other aspects, the one or more pivotable fenestrations 12 may be positioned to align with other branch arteries throughout a diseased vasculature. Additional fenestrations and scallops as disclosed here may also be included.

Figure 2:
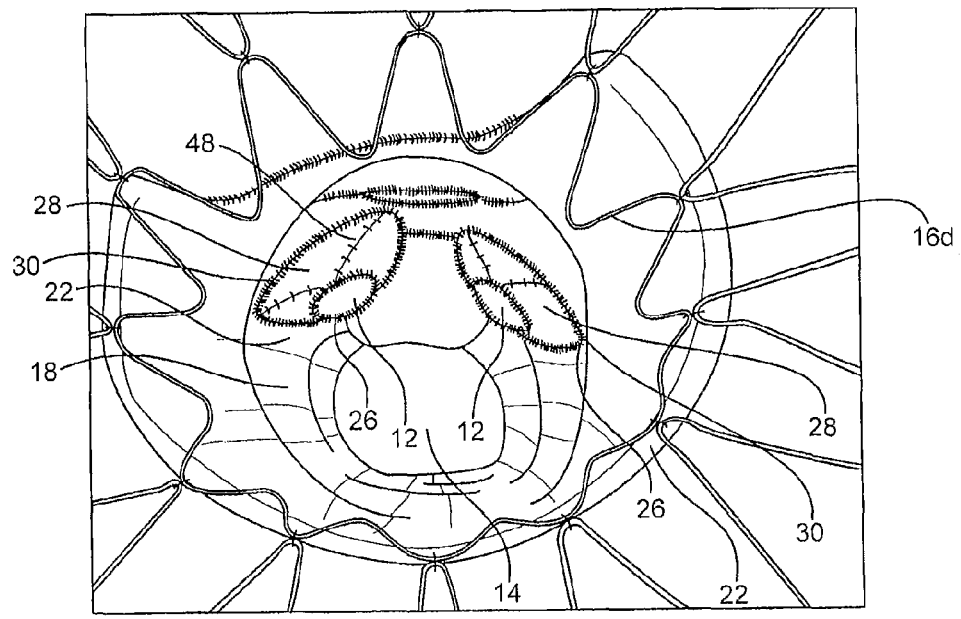
FIG. 2 is a partial and internal view of the prosthesis of FIG. 1.

FIG. 2, which is a partial internal view of the prosthesis 10 of FIG. 1, shows a view of the prosthesis 10 looking into the lumen 18 of the prosthesis 10 from the proximal end 22. As shown, pivotable fenestrations 12 extend or protrude into the lumen 18. Pivotable fenestrations 12 have an inner perimeter 26, a band 28, and an outer perimeter 30. As shown in FIG. 2, the outer perimeter 30 lies substantially flush (in the same plane) of the graft material 14, and the band 28 and the outer perimeter 30 form a hemispherical shape, such as a dome or frustoconical cone extending into the lumen 18. Although both the first and outer perimeters 26, 30 are shown as substantially circular, they may be oval, oblong or some other desired geometric shape.

Figure 3:
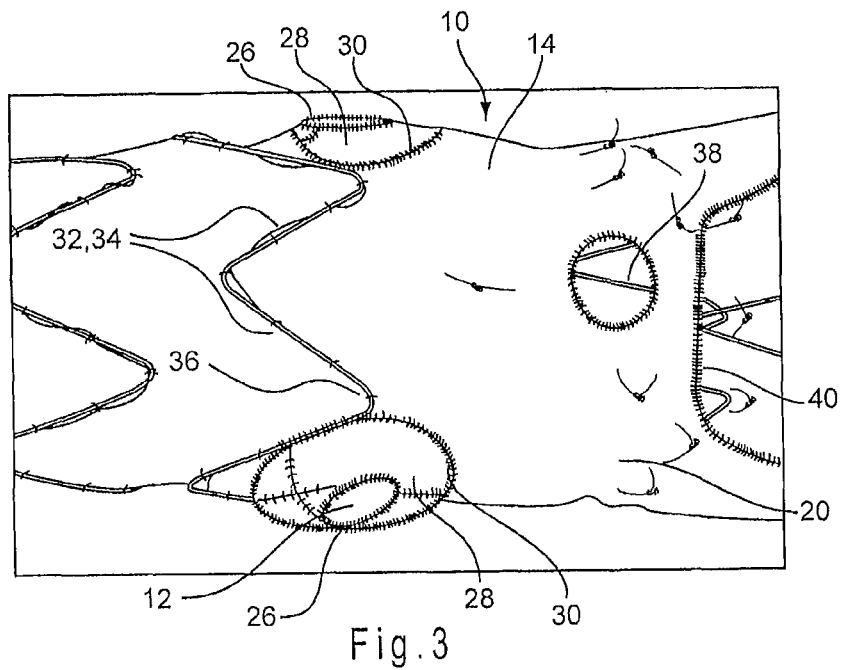
FIG. 3 shows a perspective view of a fenestrated prosthesis having pivotable fenestrations convex (external) pivotable fenestrations.
Figure 4:
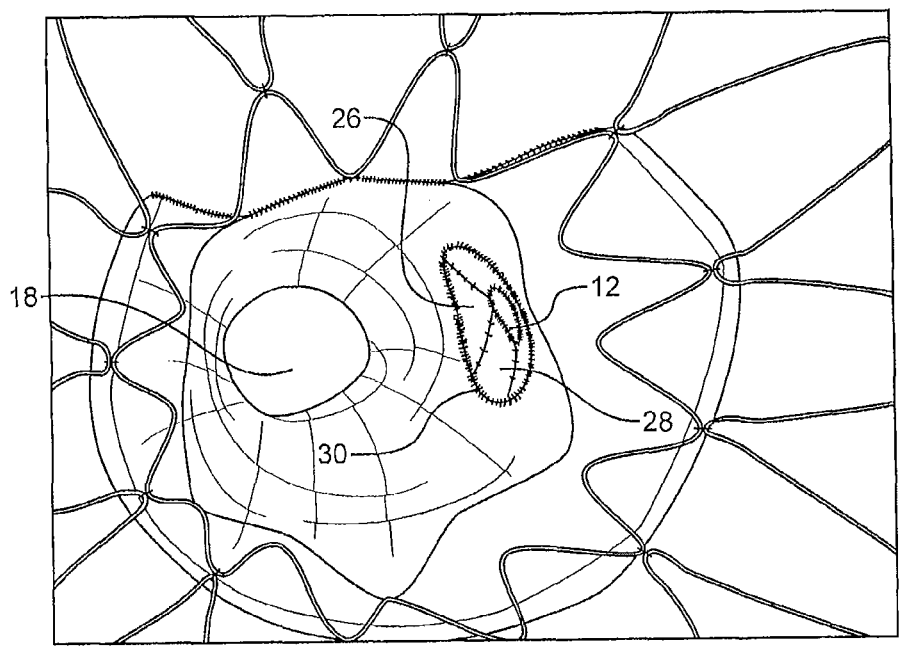
FIG. 4 is a partial and internal view of the prosthesis of FIG. 3.

FIGS. 3 and 4 show an aspect of a prosthesis 10 having externally extending pivotable fenestrations 12. FIG. 3 shows a partial view of a prosthesis 10 having two externally extending pivotable fenestrations 12 extending form opposite sides of the prosthesis 10. As with the other aspects, the fenestrations 12 have an inner perimeter 26 surrounding the fenestration, a band 28 of material surrounding the inner perimeter 26, and an outer perimeter 30 surrounding the band 28 of material. FIG. 4, which is a partial internal view of the prosthesis 10 of FIG. 3, shows a view of the prosthesis 10 of FIG. 3, looking into the lumen 18 of the prosthesis 10 from the proximal end 22. As shown, pivotable fenestrations 12 extent or protrude away from the external surface 20 of the graft material 14. The outer perimeter 30 lies substantially flush (in the same plane) of the graft material 14, and the band 28 and the outer perimeter 30 form a hemispherical shape, such as a dome, or frustoconical cone extending into the lumen 18.

Figure 6:
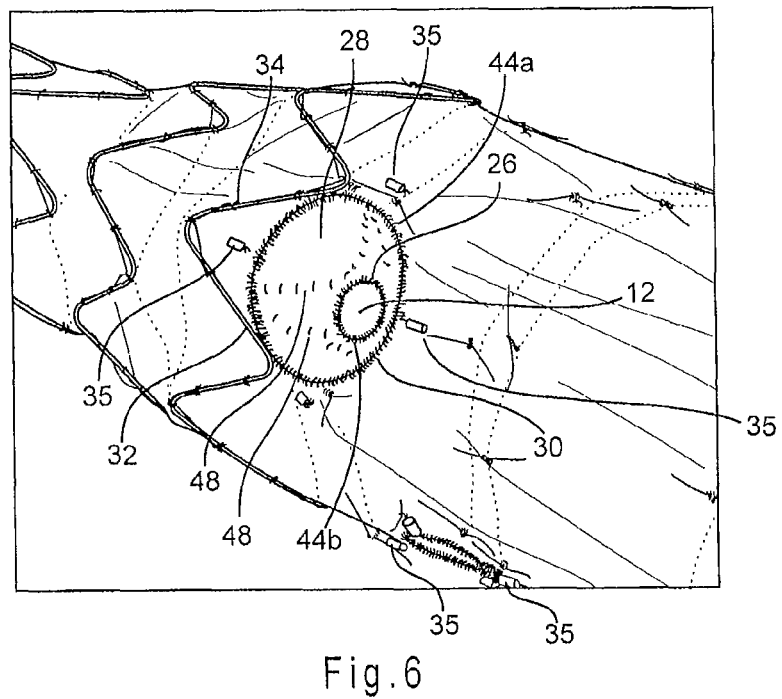
FIG. 6 is an enlarged perspective view of the pivotable fenestration shown FIG. 5.

FIGS. 5 and 6 show further aspects of a fenestrated prosthesis 10 having at least one pivotable fenestration 12. FIG. 5 shows a prosthesis 10 that is a stent graft. The prosthesis includes that has a proximal end 22, a distal end 24, a graft material 14 associated with a series of external stents 16. The prosthesis 10 further has an internal sealing stent 16d, and attachment stent 42, and a pivotable fenestration 12. FIG. 6 shows a partial close up view of the fenestration of FIG. 5. The pivotable fenestration 12 shown is an external fenestration 12 and has an inner perimeter 26 surrounding the fenestration 12, a band 28 of material surrounding the inner perimeter 26, and an outer perimeter 30 surrounding the band 26. As shown, a portion of the outer perimeter 30 lies between struts 32, 34 of the proximal most stent 16. Referring back to FIG. 5, the prosthesis 10 includes a non-pivoting fenestration 28 and a scallop 40 at the proximal end 22. As shown in these Figures and throughout the Figures, imageable markers 35, which may be viewed during and after placement of the prosthesis 10 may be placed at various locations on the prosthesis 10 to identify certain aspects of the prosthesis and their location during the implantation procedure and facilitate correct placement of the fenestrations 12, 38, scallop 40, the ends of the prosthesis and the like. For example, as shown in FIG. 6, markers 35 may be placed about the circumference of the outer perimeter 30. The markers 35 may be, for example, sewn or sutured to the graft material 14, as shown, or may be woven into the graft (not shown). The markers 35 also may be placed on the struts of one or more stents, for example, radiopaque marker tubes may be placed about one or more struts of the stent to indicate various areas of the stent graft. As shown, the markers 35 may be gold, however, any material that may be imaged by way of angiography, fluoroscopy, 3D imaging, MRI, or the like, may be suitable.

Figure 7:
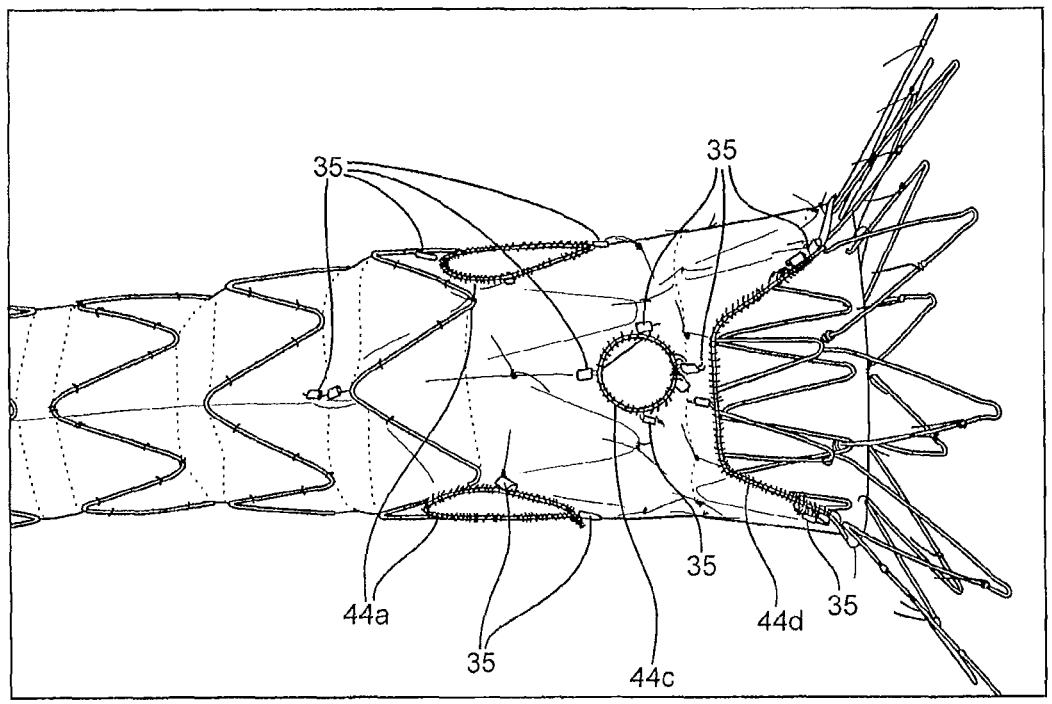
FIG. 7 shows a fenestrated prosthesis having imageable markers and reinforcement frames.

As further shown, particularly in FIGS. 6-7, the fenestrations 12, 38 and the scallop 40 may include a reinforcement frame 44a, 44b, 44c, 44d which may be sutured or otherwise attached to the graft 14. For example, in FIGS. 6-7, a reinforcement frame 44a may be positioned about the outer perimeter 30. As shown in FIG. 6, a reinforcement frame 44b may be positioned about the inner perimeter 26. As shown in FIG. 7, in particular, a reinforcement frame 44c may be provided about the non-pivoting fenestration 38, and reinforcement frame 44d may be provided about the perimeter of the scallop 40. The reinforcement frames 44a, 44b, 44c, 44d may be rings. In one preferred aspect, the reinforcement frames 44a, 44b, 44c, 44d are a wire that is sutured about the fenestration 12, 38, or scallop 40, to reinforce the fenestration or scallop. The reinforcement frames 44a, 44b, 44c, 44d may be made of any suitable material. One preferred material is a superelastic or shape memory material, such as nitinol. In another preferred embodiment, the reinforcement frames 44a, 44b, 44c, 44d may be made of radiopaque or other imageable material. In another embodiment the reinforcement frames 44a, 44b, 44c, 44d may be solid rings, or may be a wire that is looped about itself into a ring with unattached ends such that the ring may be expanded or contracted in diameter. Suitable frames are disclosed in U.S. patent application Ser. No. 10/962,632, filed Oct. 12, 2004, hereby incorporated by reference.

Figure 8:
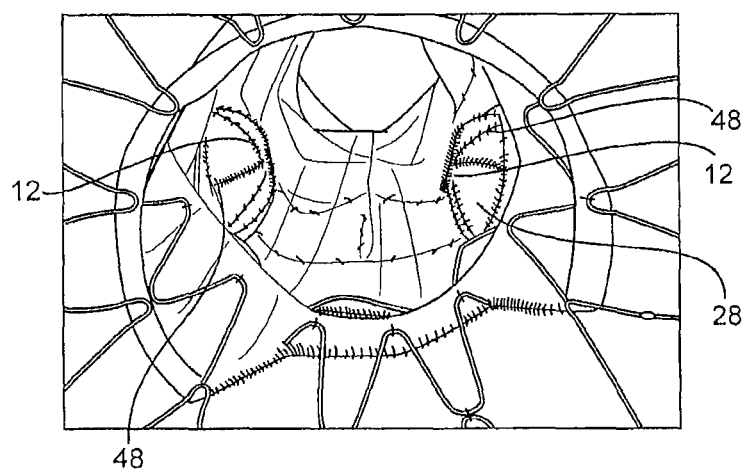
FIG. 8 is another partial and internal view of an internal pivotable fenestration.

FIG. 8 is another partial and internal view of a fenestrated prosthesis 10 having two internal pivotable fenestrations 12. As shown in this aspect, a dome-like projection or frustoconical extension is formed within the prosthesis 10. A flexible frame 48 may be disposed about or within the band 28.

As shown throughout the Figures, inner perimeter 26, band 28, and outer perimeter 30 surround the pivotable fenestration 12 to create a hemisphere shaped or frustoconical extension or protrusion. The outer perimeter 30 may be affixed to the graft material 14 by any attachment method including suturing circumferentially about an aperture disposed through graft material 14. The band 28 may be comprised of the same or different biocompatible material as the graft material 14. For example, the second biocompatible material may have greater pliability than the first biocompatible graft material used for the tubular graft body.

The band 28 is sufficiently flexible to permit the fenestration 12 to move such that a branch stent disposed in the fenestration 12 may be oriented upwardly, downwardly, laterally, diagonally and the like. In some aspects, the band has up to about 180 degrees of freedom of movement relative to the surface plane of the prosthesis 10. Accordingly, the pivotable fenestration 12 allows the prosthesis 10 to be used with a variety of patients, due to its ability to adapt to the variance in the positioning of the diseased branch vessels. For example, if a body branch vessel is or becomes offset longitudinally or axially from a pivoting fenestration 12, the pivoting fenestration 12 will pivot the branch vessel prosthesis in the necessary direction and to the necessary degree to maintain the branch vessel prosthesis in place in the branch vessel.

Figure 9:
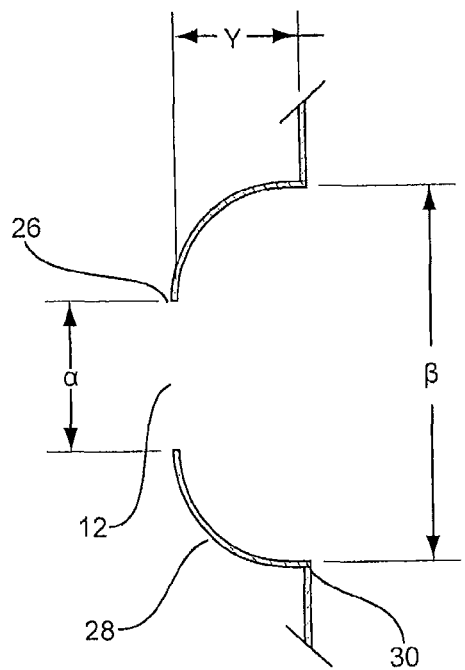
FIG. 9 is a partial, cross-sectional view of a portion of a prosthesis having a pivotable fenestration.

FIG. 9 shows a partial, cross-sectional view of a portion of prosthesis 10 having a pivotable fenestration 12, inner perimeter 26 surrounding fenestration 12, band 28 surrounding inner perimeter 26 and outer perimeter surrounding band 28. The band 28 may be tapered such that the diameter decreases throughout its depth γ. The depth γ may be determined on the amount of movement required for the pivotable fenestration 12 during use and the ability to cannulate the targeted branch vessel. As the depth γ the amount of second biocompatible material used for the band 28 must also decrease, which limits the range of motion of the pivotable fenestration 12. Furthermore, the depth γ must be large enough in order to cannulate the targeted branch vessel. The depth γ may range from 3 to 10 mm, and preferably is about 6 mm. As shown, inner perimeter 26 has a diameter α that is smaller than the diameter β of outer perimeter 30. The diameter α inner perimeter 28 may be determined based on the average size of the targeted branch vessel. In this aspect, the prosthesis 10 may be used to repair a diseased renal artery. Accordingly, the average diameter of the inner perimeter 26 may be based on the average of the diameter α of the openings to the renal arteries, or about 6 mm.

The diameter β of the outer perimeter 30 may be determined based on the desired amount of movement and the desired patency of the prosthesis 10. As the diameter β of the outer perimeter 30 changes, the range of motion also changes. As the diameter β of the outer perimeter 30 decreases, the range of motion also decreases. Additionally, the diameter β of the outer perimeter 30 must be sized to prevent interference with circumferentially adjacent struts 32, 34 of the stents 16. Hence, the diameter β of the outer perimeter 30 may be at most about 15 mm in order to accommodate stents 16. The diameters α and β combined with depth γ provide the requisite amount of surface area for band 28 for the pivotable fenestration 12 to pivot during deployment of a secondary branch prosthesis into the fenestration 12 of after deployment based on dynamic changes to the anatomy.

Figure 10:
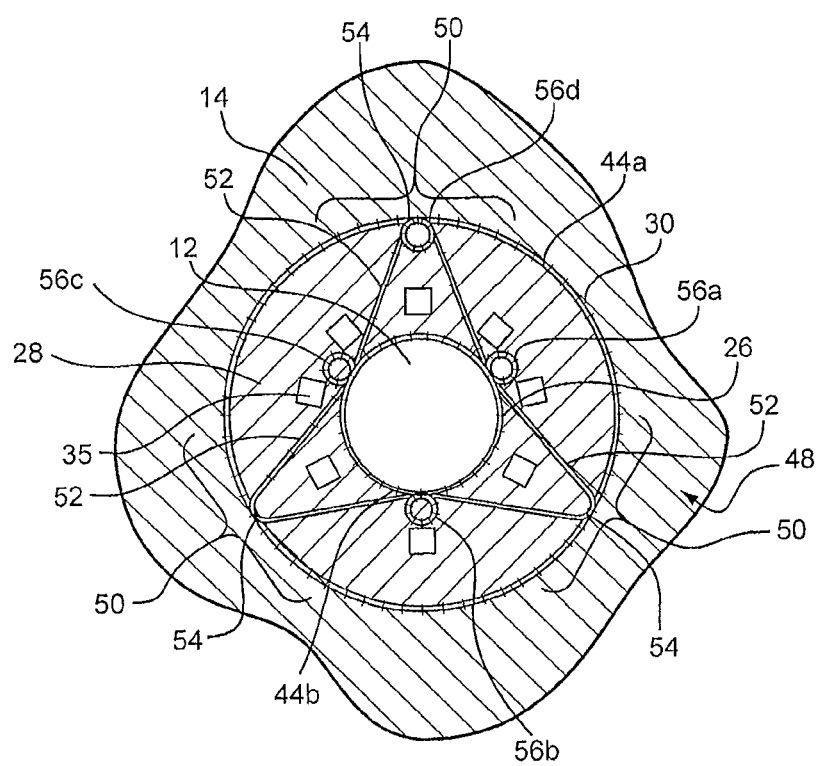
FIG. 10 shows an interior view of a pivotable fenestration where the fenestration is disposed within the lumen of the prosthesis.
Figure 11:
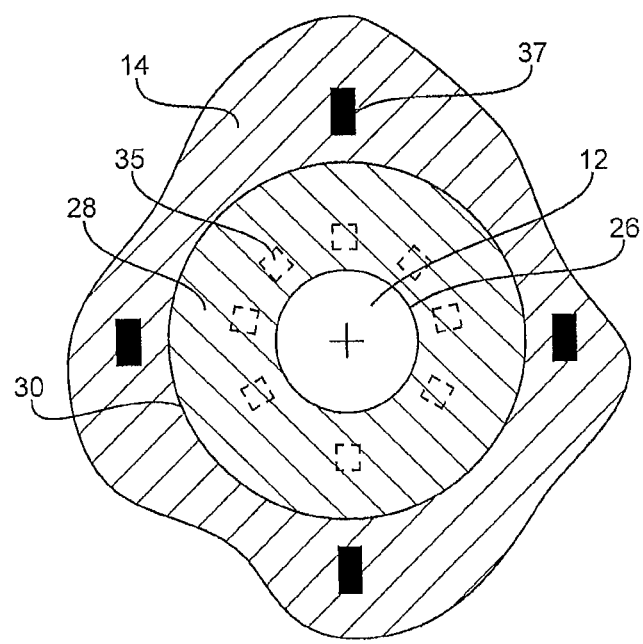
FIG. 11 shows an exterior view of a pivotable fenestration where the fenestration is disposed within the lumen of the prosthesis.

FIGS. 10 and 11 show an internal view and an external view, respectively, of a pivotable fenestration 12 in an aspect where the fenestration is disposed within the lumen 18 of the prosthesis 10. FIG. 10 shows pivotable fenestration 12, inner perimeter 26, band 28, outer perimeter 30. The inner perimeter 26 and outer perimeter 28 a reinforcement frame 44*a* is positioned about the outer perimeter 30. A reinforcement frame 44*b* is positioned about the inner perimeter 26. As discussed above, the reinforcement frames 44*a* and 44*b* may be affixed to the 26 outer perimeter 30 and inner perimeter 26 may be, for example, sewn to the outer surface 20 of the graft material 14. Markers 35 are placed around the inner perimeter 26 in order to facilitate proper placement and alignment of a branch vessel prosthesis and the pivotable fenestration 12.

As shown in FIG. 10, the band 28 may be provided with a flexible frame 48. The flexible frame 48 provides support to the band 28 and helps to maintain the overall structure of the band 28 upon deployment within the diseased vessel. The flexible frame 48 also helps to maintain the patency of the pivotable fenestration 12. The flexible frame 48 allows to the band of material to reverse orientation and independently move between an interior surface of the prosthesis 10 and an exterior surface of the prosthesis 10 while the device is being deployed. In some embodiments, a physician may alter the orientation of the band 28 during deployment of the prosthesis 10 through the use of endoluminal devices, such as a guidewire catheter. The structure of the flexible frame 48 also prevents the pivotable fenestration 12 from everting or inverting (depending on the initial configuration) once the prosthesis 10 is deployed within the diseased vessel. The flexible frame 48 may be positioned on the band 28 either on the interior or exterior surface of the band 28. In this particular aspect, the flexible frame 48 is position on the interior surface of the band 28. The flexible frame 48 comprises a continuous wire formed into a plurality of support units 50 having a generally undulating shape comprising straightened struts 52 interconnected by outwardly facing apices or bends 54. The number of support units 50 may range from about 2 support units to about 10 support units.

In a preferred aspect, the flexible frame 48 has three support units 50. For example, as shown in FIG. 10, the outwardly facing apices 54 may abut or connect to the reinforcing frame 44*a* of the outer perimeter 30. The outwardly facing apices may be, for example, sewn or sutured to reinforcing frame 44*a*. The frame 48 may be bent to form a plurality of loops 56*a*, 56*b*, 56*c*, 56*d*. Loops 56*a*, 56*b*, 56*c* are positioned in the troughs of the apices 52 of adjacent support units 50. Each loop 56*a*, 56*b*, 56*c* may abut or connect to the reinforcing frame 44*b* of the inner perimeter 26. The loops 56*a*, 56*b*, 56*c* may be, for example, sewn or sutured to reinforcing frame 44*b*. A loop 56*d* may be positioned within an apex 54 of a support unit 50. Other aspects may comprise other configurations for the flexible frame 48, including, but not limited to, spirals, may be suitable. The flexible frame 48 may be heat set into the desired configuration prior to attachment to band 28. The flexible frame 48 may be comprised of an elastic or super elastic material, for example and without limitation, nitinol.

FIG. 11 shows an exterior view of a pivotable fenestration 12 where the fenestration is disposed within the lumen of the prosthesis. The pivotable fenestration 12 has an inner perimeter 26 surrounding the fenestration 12, a band 28 surrounding the inner perimeter 26, and an outer perimeter 30 surrounding the band 28. The inner perimeter 26 and outer perimeter 28 a reinforcement frame 44*a* is positioned about the outer perimeter 30. Markers 37 may be sewn to around the circumference of the outer perimeter 30 in order to facilitate proper placement and alignment of the pivotable fenestration 12 and the targeted branch vessel.

Figure 12:
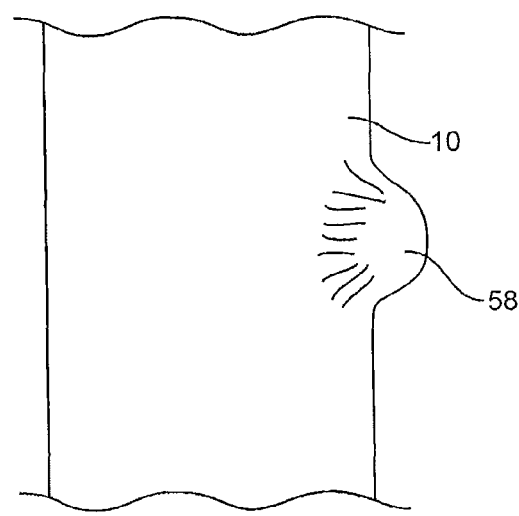
FIG. 12 is a prosthesis having a protrusion of graft material to form a fenestration and an extension.

FIG. 12 shows an embodiment of the band 28 formed from a protrusion 58 having a bubble like configuration as shown in FIG. 12, as described in co-pending U.S. patent application Ser. No. 12/548,120. The protrusion 58 is integrally formed with the body of the prosthesis 10 and is comprised of a second biocompatible graft material. The protrusion 58 may be created during the weaving process used to create the graft material 14. The prosthesis 10 may include, but is not limited to, weaves such as plain weaves, basket weaves, rep or rib weaves, twill weaves (e.g., straight twill, reverse twill, herringbone twill), satin weaves, and double weaves (e.g., double-width, tubular double weave, reversed double weave). Desirably, the weave comprises a tubular double layer weave. The fabric may be woven on a table loom, a floor loom, a jacquard loom, a counterbalance loom, a jack loom, or an upright loom. Desirably, the fabric is woven on a floor loom. The fabric may have any configuration possible, but preferably has warp and weft yarns. In one aspect, both the warp yarns and the weft yarns are textile yarns.

In order to create the protrusion 58, the number of warp yarns used while weaving the prosthesis 10 is increased in the region where the protrusion 315 is desired. While the additional warp yarns are weaved into the prosthesis 310, the number of weft yarns is kept constant. By increasing the number of warp yarns while holding the number of weft yarns constant, the second biocompatible graft material expands outwardly in the radial direction. The number of warp yarns is increased until a pre-determined diameter has been reached. Once the desired depth for the protrusion 58 is reached, the number of warp yarns introduced into the weaving apparatus is decreased until the number of warp yarns is equal to the number of weft yarns used to form the remainder of the prosthesis 10. A fenestration may be created through the protrusion 58 by applying heat to the center of the protrusion 10. Reinforcing frames may be added about the fenestration and adjacent to and surrounding the protrusion 58 to form the inner and outer perimeters 26, 30 of the prosthesis 10. Further, a flexible frame 48 may be attached to the protrusion 58 to maintain it in its desired extended configuration.

Figure 13:
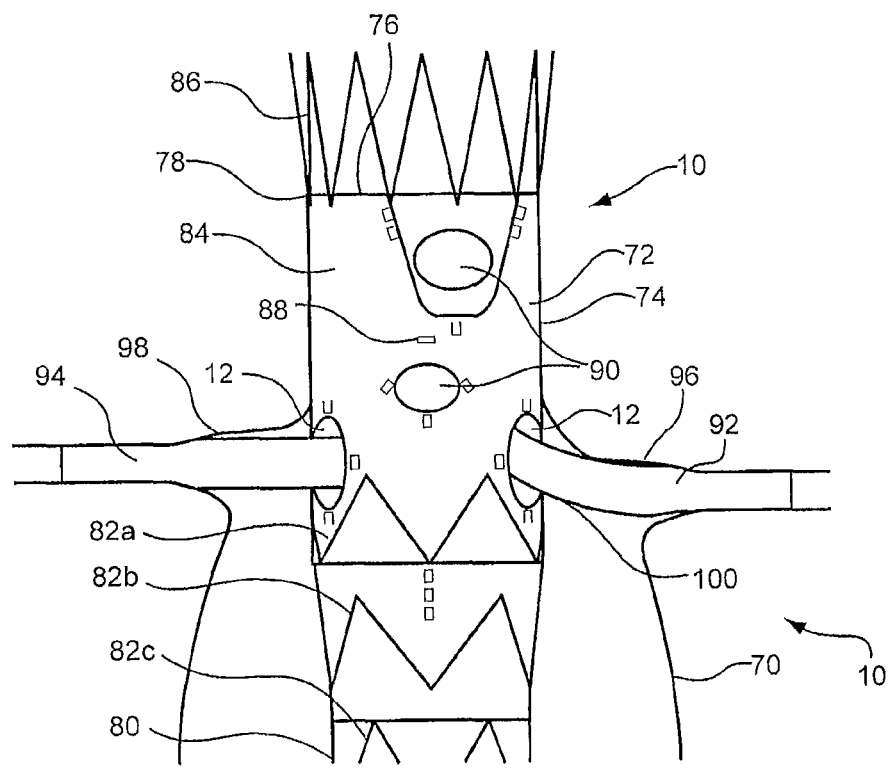
FIG. 13 is a fenestrated prosthesis that has been deployed within a diseased vessel, such as the aorta, where branch vessel prostheses are deployed within the branch vessels.

FIG. 13 depicts an exemplary prosthesis that has been deployed within a diseased vessel 70, such as the aorta. The prosthesis 10 comprises a tubular graft 72 having a sidewall 74 and a lumen 76 disposed longitudinally therein. The prosthesis 10 includes a first end 78 and a second end 80. The tubular graft 72 includes a plurality of rows 82*a*, 82*b*, 82*c* of expandable stents circumferentially aligned affixed to the outer surface 84 of the tubular graft 72. A sealing stent 86 may be affixed to the first end 78 of the tubular graft 72 within the interior surface of the graft 72. The sealing stent 86 may be attached to the first end 78 of the tubular graft 72 by any attaching mechanism, for example and without limitation, suturing. Radiopaque markers 88 may be placed on the tubular graft 72 in order to assist with proper alignment of the tubular graft 72 when deployed within a patient. Fenestrations 90 may be disposed through the tubular graft 72. The distal end (not shown) of the prosthesis 10 may be bifurcated.

The tubular graft 72 also includes two internal pivotable fenestrations 12 that are in communication with the lumen 76. The tubular graft 72 may be preloaded onto a delivery device for deployment within a patient. The delivery device includes a sheath over the tubular graft 72 to keep the tubular graft 72 in a compressed state prior to deployment. The delivery device is placed over a guide wire and after checking the appearance and orientation of the device under x-ray, guide wires for each fenestration 12 are loaded through side ports in the handle of the delivery device. The delivery device is introduced over the guide wire, and advanced until a tapered tip of the delivery device is in the femoral artery and the radiopaque markers indicating the fenestrations 12 are at a level of the appropriate arteries. A sheath is advanced over the guide wire for each fenestration 12 through each side port on the handle of the device. Once the sheaths for the fenestrations 12 are in position, the tubular graft 72 can be advanced to its correct position and orientation for deployment. The tubular graft 72 is deployed by withdrawing the sheath covering the graft over the pusher. The operator can perform angiography and adjust the placement of the tubular graft 72 if necessary. Deployment is continued until the tubular graft 72 is fully unsheathed. The sheaths for the fenestrations 12 are advanced over the wires until they are at a level of the lower margin of the fenestration 12. The sheaths for the fenestrations 12 are punctured and a guide wire is advanced through each sheath. A catheter is advanced over the guide wires, and once the catheters are in the target vessels, a stiffer wire replaces the guide wire. The sheaths for the fenestrations 12 are then advanced into the target vessels and branch vessel prostheses are advanced through the sheath and placed in the desired position.

FIG. 13 illustrates in accordance with the procedure described above branch vessel prosthesis deployed through each of the two fenestrations 12. Branch vessel prostheses 92, 94 are formed from biocompatible materials and may comprise covered stents. Alternatively, they may comprise bare stents. The covered or bare stents may be either self-expanding or balloon expandable. In one aspect the branch vessel stent may have both self expanding and balloon expandable components. For example, the branch vessel stent may have an end not shown for placement within the fenestration this is upon deployment, either self-expanding or by balloon expansion. If the branch vessel stent is a covered stent, the graft material used may comprise one or more of the biocompatible materials are discussed above.

As shown in FIG. 13, the branch vessel prostheses 92, 94 are deployed into branch vessels 96, 98 such as the right and left renal arteries. As shown in Figure, the right opening 100 is not completely aligned with the right branch vessel 92. Particularly, the right branch vessel 96 is positioned lower than the corresponding left branch vessel 98. To accommodate placement of the branch vessel prosthesis 92 into the right branch vessel 96, the pivotable fenestration 12 provides the requisite flexibility and ability to pivot required for the branch vessel prosthesis 92 to deploy into the desired position.

Figure 14:
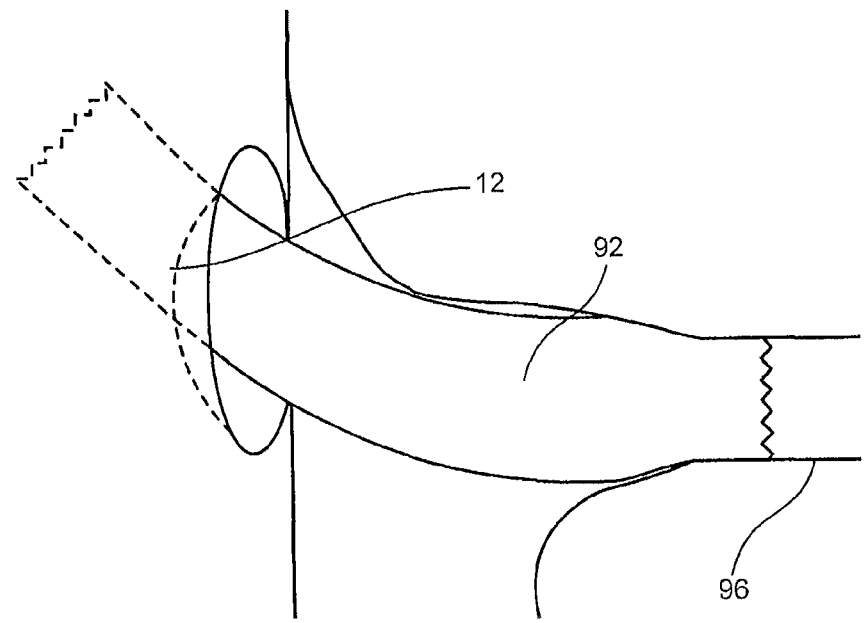
FIG. 14 shows a branch vessel prosthesis deployed in a secondary branch vessel, where the branch vessel prosthesis is deployed in a right branch vessel positioned lower than its corresponding left branch vessel.
Figure 15:
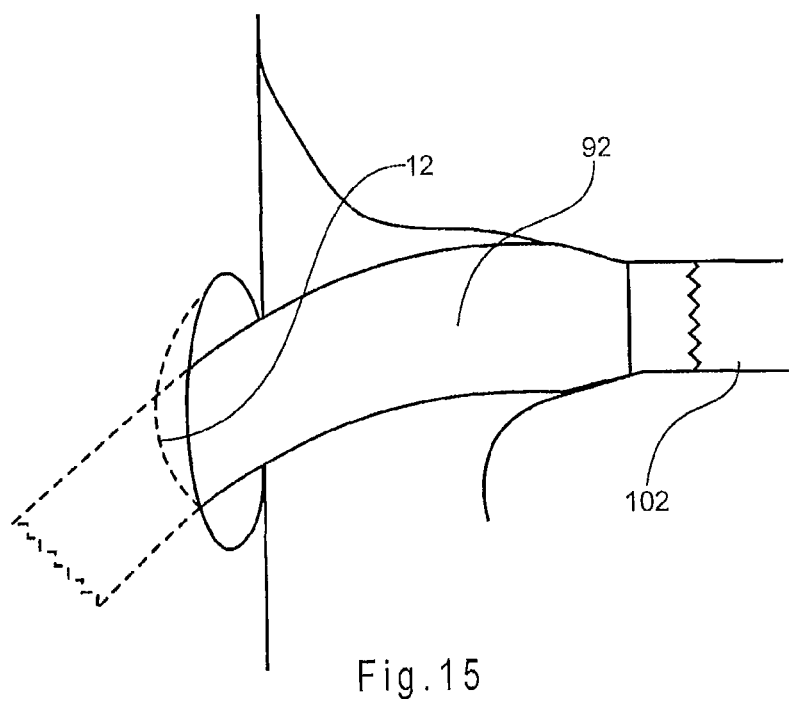
FIG. 15 shows a branch vessel prosthesis deployed in a secondary branch vessel, where the branch vessel prosthesis is deployed in a right branch vessel positioned higher than its corresponding left branch vessel.

FIGS. 14 and 15 show a branch vessel prosthesis 92 deployed in a secondary branch vessel in greater detail. As shown in FIG. 14, the branch vessel prosthesis 92 is deployed within the right branch vessel 96, which is positioned lower than its corresponding left branch vessel. Alternatively, as shown in FIG. 15, the branch vessel prosthesis 92 is deployed within the right branch vessel 102, which is positioned higher than its corresponding left branch vessel. The pivotable fenestration 12 allows for pivoting motion to accommodate the offset position of the right branch vessel 98, 102 and provide access to the right branch vessel 96, 102 through the use of a delivery device, such as a catheter.

Once a catheter is placed within right branch vessel 96, 102, the branch vessel prosthesis 92 may be deployed within the right branch vessel 96, 102. The branch vessel prosthesis 92 may be balloon expandable or self-expandable. In this aspect, the branch vessel prosthesis 92 is balloon expandable. Once the secondary branch prosthesis 146 is deployed in the right branch vessel 96, 102, the end of the branch vessel prosthesis 92 remaining within the interior surface of the prosthesis 10 may be flared in order to provide a proper seal between the fenestration 12 and the branch vessel 96, 102.

Referring now to FIGS. 16-19, an alternative endoluminal prosthesis 200 is shown and described. The prosthesis 200 comprises a graft 214 having a tubular body comprising proximal and distal ends 222 and 224, and a lumen 218 extending therebetween.

The prosthesis 200 comprises a valve replacement 260 disposed between the proximal end 222 and the distal end 224 of the graft 214. In one example, the artificial valve 260 can be coupled to the graft 214 with suture.

In one non-limiting example, the valve replacement may comprise an aortic valve designed to replace the function of the recipient's native damaged or poorly performing aortic valve. In other examples, the prosthesis 200 may be deployed in other arterial locations, i.e., other than the aortic sinus and ascending aorta, or alternatively may be deployed in a patient's venous system, or any suitable duct, passageway or vessel.

Figure 17A:
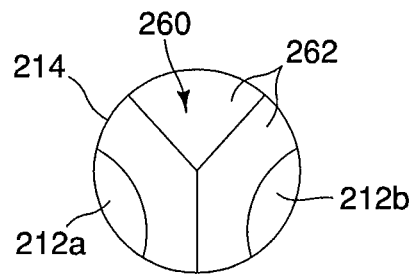
FIGS. 17A-17B are, respectively, top and bottom views of the endoluminal prosthesis of FIG. 16.
Figure 17B:
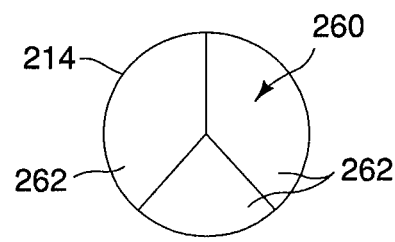

In the non-limiting example of an aortic valve, the artificial valve 260 may be located at the proximal end 222 of the graft 214, closest to the heart. The artificial valve 260 preferably includes one or more leaflets 262, as shown in FIGS. 17A-17B. In this non-limiting example, the artificial valve 260 includes three leaflets 262, though only two leaflets may be used in a "bicuspid" arrangement. The leaflets are arranged in the prosthesis such that the leaflets mimic a naturally occurring aortic valve. The artificial valve 260 "opens" to allow blood flow when the pressure on the proximal side of the artificial valve 260 is greater than pressure on the distal side of the artificial valve. Thus, the artificial valve 260 regulates the unidirectional flow of fluid from the heart into the aorta.

The leaflets of the artificial valve 260 can be fabricated from any at least substantially biocompatible material including such materials as polyester fabrics, polytetrafluoroethylene (PTFE), expanded PTFE, and other synthetic materials known to those of skill in the art. Preferably, the leaflets are fabricated from naturally occurring biomaterials. The leaflets can include a derived collagen material, such as an extracellular matrix. The extracellular matrix can be small intestinal submucosa, stomach submucosa, pericardium, liver basement membrane, urinary bladder submucosa, tissue mucosa, dura mater, or the like.

The prosthesis 200 further comprises at least one stent coupled to the graft 214 that has a contracted delivery state and further has an expanded state for maintaining patency within a portion of the graft. In the exemplary embodiment depicted in FIGS. 16 and 20, five exemplary stents 216a-216e are provided. As described with respect to the stents 16 above, the stents 216 may be placed on the external surface and/or internal surface of the graft 214. Like the stents 16 described above, the exemplary stents 216 of the prosthesis 200 comprise zig zag stents, and may be either self-expanding or balloon expandable.

Figure 16:
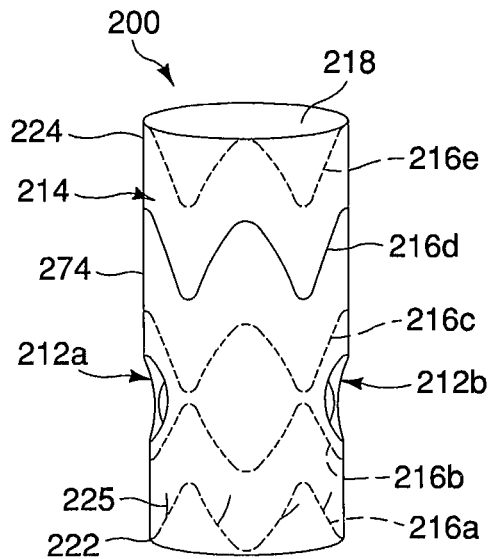
FIG. 16 is a side view of an alternative endoluminal prosthesis comprising a valve replacement.
Figure 20:
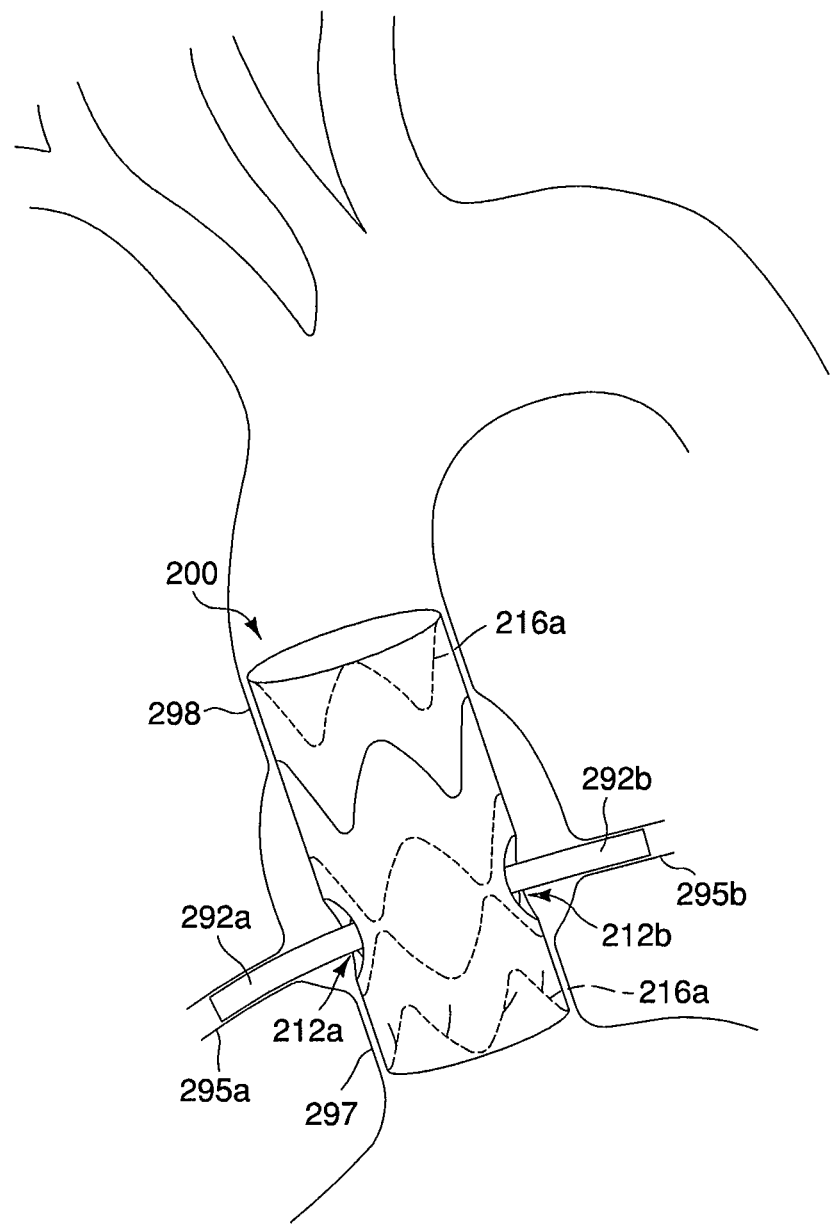
FIG. 20 is a schematic view of illustrating deployment of the endoluminal prosthesis of FIG. 16 in a patient's anatomy.

In the embodiment of FIG. 16, a first stent 216a is located at the proximal end of the graft 214. In use, the first stent 216a overlaps with an aortic annulus 297, as shown in FIG. 20. The first stent may comprise a radial force configured to facilitate fixation within the aortic annulus 297 and prevent migration of the proximal end 222 of the graft 214. One or more barbs 225 may be coupled to the first stent 216a to reduce migration of the prosthesis 200.

In the example of FIG. 16, the endoluminal prosthesis 200 comprises second and third z-stents 216b and 216c, which are coupled to the graft 214 such that the distal apices of the second stent 216b are aligned with the proximal apices of the third stent 216c. At least one fenestration 212 is positioned between a proximal apex of the second stent 216b and a distal apex of the third stent 216c. The fifth stent 216e may be configured to engage a healthy portion of a patient's ascending aorta 298, as depicted in the deployed state of FIG. 20.

The endoluminal prosthesis 200 further comprises at least one fenestration 212 disposed in a sidewall 274 of the graft 214. In the embodiment of FIGS. 16-20, first and second fenestrations 212a and 212b are disposed in the sidewall 274 at locations distal to the valve replacement 260, as seen in the top view of FIG. 17A.

The first and second fenestrations 212a and 212b preferably are provided in accordance with the fenestrations 12 described in detail above. Accordingly, at least one of the fenestrations 212a and 212b, and preferably each fenestration, is pivotable in any direction away from an axis perpendicular to a longitudinal axis of the prosthesis. Each of the fenestrations 212a and 212b may comprise the first perimeter, the band of flexible material, and the second perimeter described in detail above. As described above, the band of material of the fenestrations 212a and 212b may have a concave or convex orientation relative to the surface of the graft 214. Further, the band of material may be configured to independently move between an interior surface of the graft 214 and an exterior surface of the graft 214.

In the non-limiting example of FIGS. 16-20, the first and second fenestrations are disposed in graft 214 at locations between about 90 and about 270 degrees apart, though the positioning may be greater or less. In the deployed state, a first branch vessel prosthesis 292a extends between the first fenestration 212a and a first coronary artery 295a in a deployed state, and a second branch vessel prosthesis 292b extends between the second fenestration 212b and a second coronary artery 295b, as depicted in FIG. 20. The branch vessel prostheses 292a and 292b may be provided in accordance with the branch vessel prostheses 92 and 94 of FIG. 13 above. Moreover, delivery and deployment of the graft 214, and the branch vessel prostheses 292a and 292b, may be provided in accordance with delivery and deployment of the graft 14 and the branch vessel prostheses 92 and 94, as outlined with respect to FIG. 13 above.

In the embodiment of FIGS. 16-20, the branch vessel prostheses 292a and 292b are deployed into the right and left coronary arteries 292a and 292b. Advantageously, if the first and second fenestrations 212a and 212b are not exactly aligned with the coronary arteries for any reason, such as variable patient anatomy, then the pivotable fenestrations 212a and 212b provide the requisite flexibility and ability to pivot so that the branch vessel prostheses 292 and 294 to deploy into the desired position.

Figure 18:
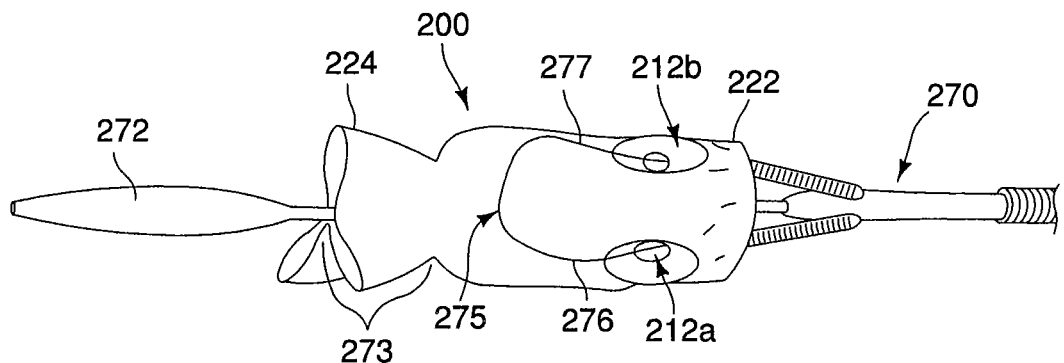
FIGS. 18 and 19 are side views of an exemplary delivery system that may be used to deliver the endoluminal prosthesis of FIG. 16.

In the examples of FIGS. 16-20, the deployment of the prosthesis 200 into the state shown in FIG. 20 may be achieved in different manners. In one example, the deployment may be made using a transapical or transeptal approach, in which case the prosthesis 200 may be secured to an exemplary delivery system 270 as shown in FIG. 18. In the transapical or transeptal approach, an atraumatic tip 272 of the delivery system is advanced in an antegrade fashion, i.e., in a direction from the aortic annulus 297 towards the ascending aorta 298.

Figure 19:
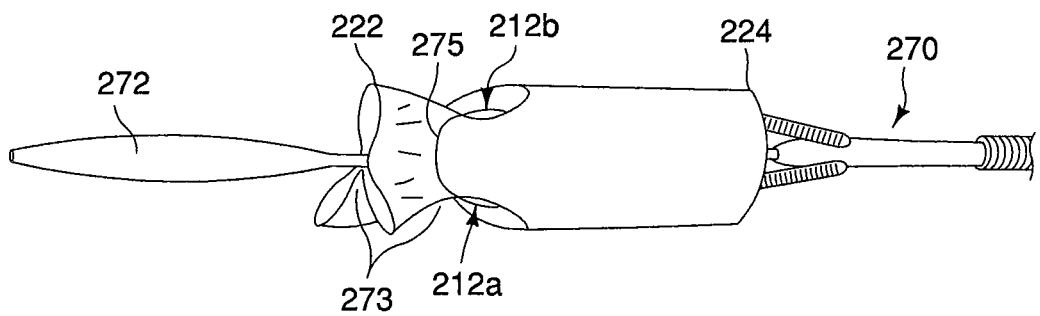

In another example, the deployment may be made using a femoral, carotid, subclavian or axiliary approach, in which case the prosthesis 200 may be secured to the exemplary delivery system 270 as shown in FIG. 19. In this approach, the atraumatic tip 272 of the delivery system 270 is advanced in a retrograde fashion, i.e., in a direction from the ascending aorta 298 towards the aortic annulus 297. In either delivery approach, as shown in FIGS. 18-19, the graft 214 may comprise one or more regions 213 that are radially restrained.

Further, the prosthesis 200 may be provided as part of a preloaded system that includes a guide wire 275. In this example, a first end segment 276 of the guide wire 276 may enter the lumen 218 through a proximal or distal end of the prosthesis 200, depending on the delivery orientation of the prosthesis shown in FIG. 18 as compared to FIG. 19. The first end segment 276 exits the graft 214 through the first fenestration 212a. An intermediate segment of the guide wire 275 may extend external of the graft 214 and reenter the lumen 218 of the prosthesis 200 through the second fenestration 212b. A second end segment 277 of the guide wire 275 may extend distally within the lumen 218 and may extend distally to the distal end of the delivery device 270. The first end segment 276 of the guide wire 275 may enable introduction of the first branch prosthesis 292a into the first fenestration 212a to couple the prosthesis 200 to the right coronary artery, and the second end segment 277 of the guide wire 277 may enable introduction of the second branch prosthesis 292b into the second fenestration 2212b to couple the prosthesis to the left coronary artery.

Further details of a such preloaded wire, and how it may facilitate deployment of stent-grafts into branch vessels, are described in further detail in U.S. Provisional Patent Application Ser. No. 61/579,027, which is hereby incorporated by reference in its entirety. While one exemplary delivery system has been shown, it will be appreciated that a number of delivery systems and techniques may be used to deploy the prosthesis 200.

As noted above, while one exemplary use of the prosthesis 200 has been shown with regard to the aortic sinus and ascending aorta, the prosthesis 200 alternatively may be deployed in other parts of a patient's arterial or venous system, or any suitable duct, passageway or vessel.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. An endoluminal prosthesis comprising:
a graft having a tubular body comprising proximal and distal ends;
a valve replacement disposed between the proximal and distal ends of the graft;
at least one stent coupled to the graft, the at least one stent having a contracted delivery state and an expanded state for maintaining patency within a portion of the graft;
at least one fenestration disposed in a sidewall of the graft at a location distal to the valve replacement;
a first perimeter having a first diameter and surrounding the at least one fenestration;
a band of flexible material attached to and surrounding the first perimeter and having a flexible frame; and
a second perimeter attached to and surrounding the band of flexible material and having a second diameter greater than the first perimeter diameter;
where the band of material has a first diameter substantially the same as the first perimeter diameter and a second diameter substantially the same as the diameter of the second perimeter, and where the diameter of the band of material decreases in a direction away from the surface of the graft from the second perimeter to the first perimeter,
wherein the band of material is configured to independently move between an interior surface of the graft and an exterior surface of the graft, and
wherein the flexible frame extends about a surface of the band from the first perimeter to the second perimeter.

2. The endoluminal prosthesis of claim 1 wherein the at least one fenestration is pivotable in any direction away from an axis perpendicular to a longitudinal axis of the prosthesis.

3. The endoluminal prosthesis of claim 1 wherein the band of material has a concave or convex orientation relative to the surface of the graft.

4. The endoluminal prosthesis of claim 1 wherein first and second fenestrations are disposed in the graft at locations between about 90 and about 270 degrees apart.

5. The endoluminal prosthesis of claim 4 further comprising a first branch vessel prosthesis extending between the first fenestration and a right coronary artery in a deployed state, and a second branch vessel prosthesis extending between the second fenestration and a left coronary artery in the deployed state.

6. The endoluminal prosthesis of claim 1 wherein first and second z-stents are coupled to the graft such that the distal apices of the first stent are aligned with the proximal apices of the second stent, and the at least one fenestration is positioned between a proximal apex of the first stent and a distal apex of the second stent.

7. The endoluminal prosthesis of claim 1 wherein the valve replacement comprises an artificial valve having a tricuspid shape.

8. The endoluminal prosthesis of claim 1 wherein the valve replacement is located at the proximal end of the graft, and one or more barbs extend radially outward from the proximal end of the graft.

9. An endoluminal prosthesis comprising:
a graft having a tubular body comprising proximal and distal ends;
a valve replacement disposed between the proximal and distal ends of the graft;
at least one stent coupled to the graft, the at least one stent having a contracted delivery state and an expanded state for maintaining patency within a portion of the graft;
at least one fenestration disposed in a sidewall of the graft and pivotable in any direction away from an axis perpendicular to a longitudinal axis of the prosthesis;
a first perimeter having a first diameter and surrounding the at least one fenestration;
a band of flexible material attached to and surrounding the first perimeter and having a flexible frame; and
a second perimeter attached to and surrounding the band of flexible material and having a second diameter greater than the first perimeter diameter;
where the band of material has a first diameter substantially the same as the first perimeter diameter and a second diameter substantially the same as the diameter of the second perimeter, and where the diameter of the band of material decreases in a direction away from the surface of the graft from the second perimeter to the first perimeter,
wherein the band of material is configured to independently move between an interior surface of the graft and an exterior surface of the graft, and
wherein the flexible frame extends about a surface of the band from the first perimeter to the second perimeter.

10. The endoluminal prosthesis of claim 9 where the at least one fenestration is disposed at a location distal to the valve replacement.

11. The endoluminal prosthesis of claim 9 wherein the band of material has a concave or convex orientation relative to the surface of the graft.

12. The endoluminal prosthesis of claim 9 wherein first and second fenestrations are disposed in the graft at locations between about 90 and about 270 degrees apart.

13. An endoluminal prosthesis comprising:
a graft having a tubular body comprising proximal and distal ends;
a valve replacement disposed between the proximal and distal ends of the graft;
at least one stent coupled to the graft, the at least one stent having a contracted delivery state and an expanded state for maintaining patency within a portion of the graft;
first and second fenestrations disposed in the graft at locations between about 90 and about 270 degrees apart;
a first branch vessel prosthesis extending between the first fenestration and a right coronary artery in a deployed state, and a second branch vessel prosthesis extending between the second fenestration and a left coronary artery in the deployed state;
a first perimeter having a first diameter and surrounding the first fenestration;
a band of flexible material attached to and surrounding the first perimeter and having a flexible frame; and a second perimeter attached to and surrounding the band of flexible material and having a second diameter greater than the first perimeter diameter;

where the band of material has a first diameter substantially the same as the first perimeter diameter and a second diameter substantially the same as the diameter of the second perimeter, and where the diameter of the band of material decreases in a direction away from the surface of the graft from the second perimeter to the first perimeter, wherein the band of material is configured to independently move between an interior surface of the graft and an exterior surface of the graft, and wherein the flexible frame extends about a surface of the band from the first perimeter to the second perimeter.

14. The endoluminal prosthesis of claim 13 wherein the first and second fenestrations are disposed at a location distal to the valve replacement.

15. The endoluminal prosthesis of claim 13 wherein each of the first and second fenestrations are pivotable in any direction away from an axis perpendicular to a longitudinal axis of the prosthesis.

16. The endoluminal prosthesis of claim 13 wherein the valve replacement comprises an artificial valve having a tricuspid shape.

* * * * *